(12) United States Patent
Mavrinac

(10) Patent No.: US 11,389,320 B2
(45) Date of Patent: Jul. 19, 2022

(54) MALE EXTERNAL CATHETER

(71) Applicant: Brian Mavrinac, Middletown, NJ (US)

(72) Inventor: Brian Mavrinac, Middletown, NJ (US)

(*) Notice: Subject to any disclaimer, the term of this patent is extended or adjusted under 35 U.S.C. 154(b) by 340 days.

(21) Appl. No.: 16/533,172

(22) Filed: Aug. 6, 2019

(65) Prior Publication Data
US 2021/0038423 A1 Feb. 11, 2021

(51) Int. Cl.
A61F 5/443 (2006.01)
A61F 5/453 (2006.01)

(52) U.S. Cl.
CPC ............. A61F 5/443 (2013.01); A61F 5/453 (2013.01)

(58) Field of Classification Search
CPC ............ A61F 5/443; A61F 5/453; A61F 5/44
See application file for complete search history.

(56) References Cited

U.S. PATENT DOCUMENTS

| | | | |
|---|---|---|---|
| 3,200,415 A | 8/1965 | Breece | |
| 3,292,626 A | 12/1966 | Schneider | |
| 3,353,538 A | 11/1967 | Carrigan | |
| 4,246,909 A * | 1/1981 | Wu | A61M 25/00 600/575 |
| 4,626,250 A | 12/1986 | Schneider | |
| 5,730,736 A * | 3/1998 | Sawers | A61F 5/443 604/332 |
| 6,849,070 B1 * | 2/2005 | Hansen | A61F 5/44 604/328 |
| 7,896,857 B2 | 3/2011 | Kay | |
| 7,947,025 B2 | 5/2011 | Buglino | |
| 8,551,062 B2 | 10/2013 | Kay | |
| 9,119,727 B2 | 9/2015 | Hannan | |

(Continued)

FOREIGN PATENT DOCUMENTS

| | | |
|---|---|---|
| CN | 106983594 A * | 7/2017 |
| EP | 0032138 A2 | 7/1981 |

(Continued)

OTHER PUBLICATIONS

I. Alnadhari, O. Abdeljaleel, O. Ali, A. Shamsodini, & M. Salah, Urethral Catheterization of Buried Penis in Obese Patients: a Novel Technique and Literature Review, National Center for Biotechnology Information (Oct. 28, 2018), https://www.ncbi.nlm.nih.gov/pubmed/30030726.

(Continued)

Primary Examiner — Tatyana Zalukaeva
Assistant Examiner — Hans Kaliher
(74) Attorney, Agent, or Firm — Ellenoff Grossman & Schole LLP; John C. Stellabotte

(57) ABSTRACT

An apparatus and associated methods relate to an external catheter configured with a urine collection bag having a semi-rigid and flexible internal tube adapted to permit fluid engagement with urine streaming from a patient, in a manner that does not require precisely locating a patient's buried, retracted or retractive penis supported by secure connection to the patient coincident to the outer circumference of the internal tube with an adhesive having a removable non-adhesive backing to prevent the dislodging or misplacement of the external catheter or obstruction of the flow of urine and the secure attachment of the tube to a transparent urine collection bag permitting visualization of the inner contents of the bag.

15 Claims, 3 Drawing Sheets

(56) References Cited

U.S. PATENT DOCUMENTS

| | | | |
|---|---|---|---|
| 9,254,218 B2 | 2/2016 | Newton, Jr. | |
| 9,788,992 B2 | 10/2017 | Harvie | |
| 10,016,299 B2 | 7/2018 | Pierson | |
| 10,022,261 B1* | 7/2018 | Harders | A61F 5/453 |
| 2006/0100607 A1 | 5/2006 | Brown | |
| 2010/0298789 A1* | 11/2010 | Santimaw | A61F 5/445 |
| | | | 604/319 |
| 2018/0098877 A1* | 4/2018 | Pierson | A61F 5/4405 |
| 2019/0247222 A1* | 8/2019 | Ecklund | A61F 5/443 |

FOREIGN PATENT DOCUMENTS

| | | | |
|---|---|---|---|
| EP | 0119143 A1 | 9/1984 | |
| EP | 0335564 A1 | 10/1989 | |
| EP | 2464411 B1 | 1/2016 | |
| GB | 2545967 A | 7/2017 | |

OTHER PUBLICATIONS

Mikel Gray, Claudia Skinner, & Wendy Kaler, External Collection Devices as an Alternative to the Indwelling Urinary Catheter, National Center for Biotechnology Information (May 13, 2016), https://www.ncbi.nlm.nih.gov/pmc/articles/PMC4870965/.

Men's Liberty; https://www.mensliberty.com/product/mens-liberty/ (webpage accessed Aug. 19, 2019).

Hollister; Male Urinary Pouch External Collection Device; https://www.hollister.com/en/products/Continence-Care-Products/Urine-Collectors/Urine-Collection-Accessories/Male-Urinary-Pouch-External-Collection-Device.

International Search Report for PCT Patent Application No. PCT/US2020/044929, dated Nov. 12, 2020.

Written Opinion of the International Searching Authority for PCT Patent Application No. PCT/US2020/044929, dated Nov. 12, 2020.

* cited by examiner

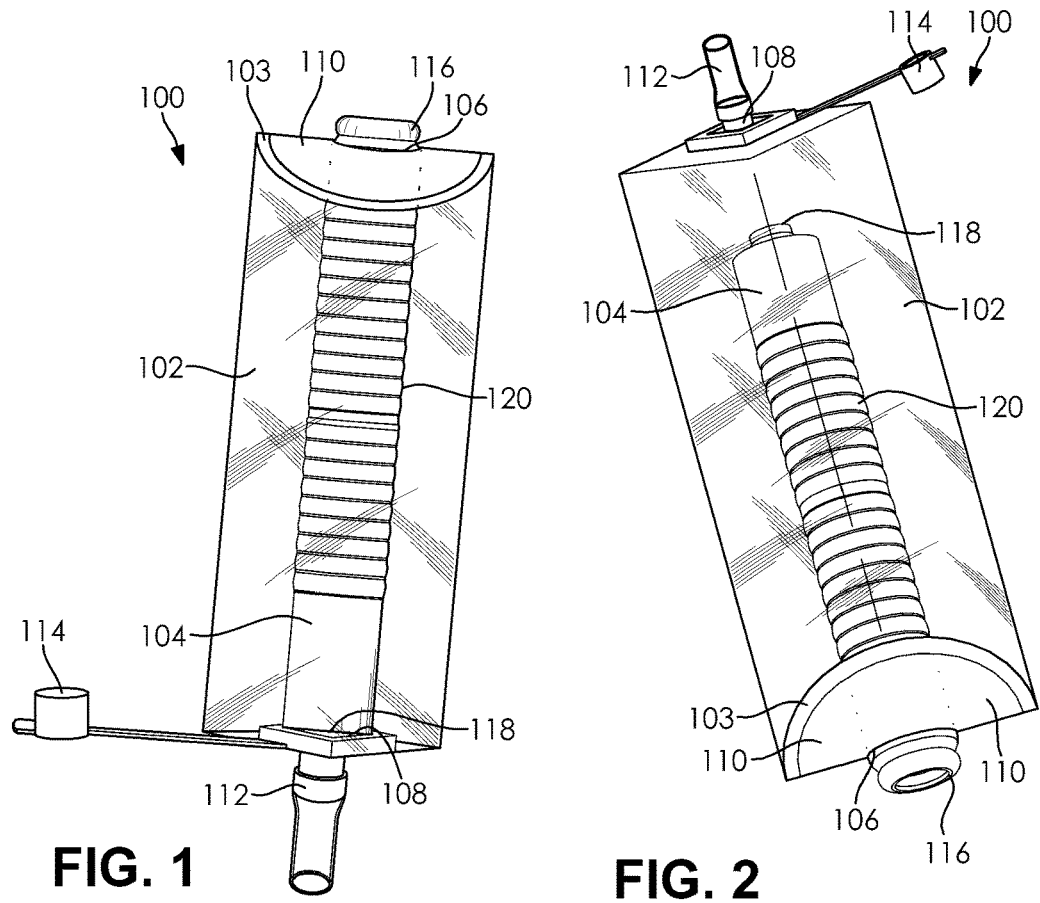
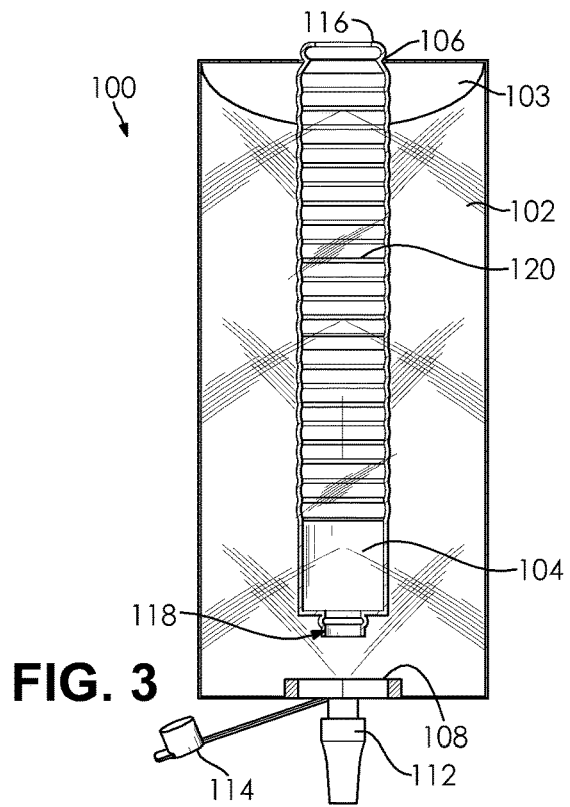

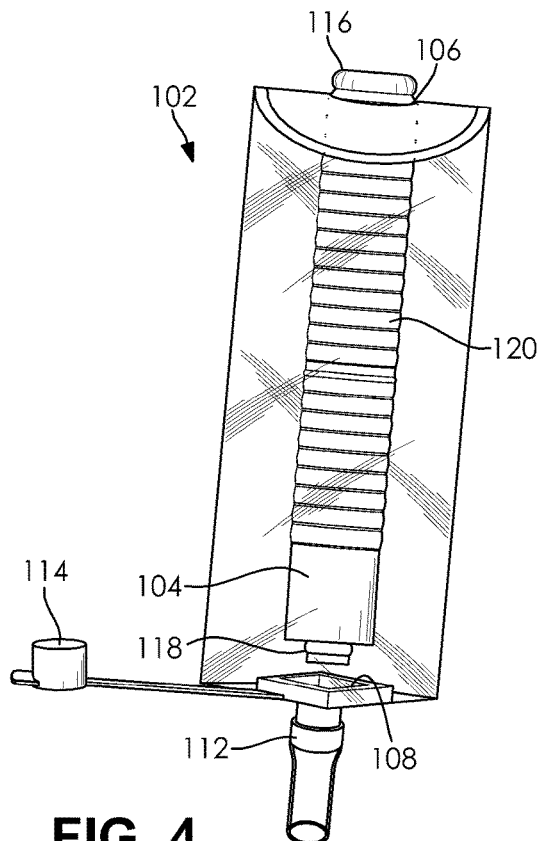
FIG. 4
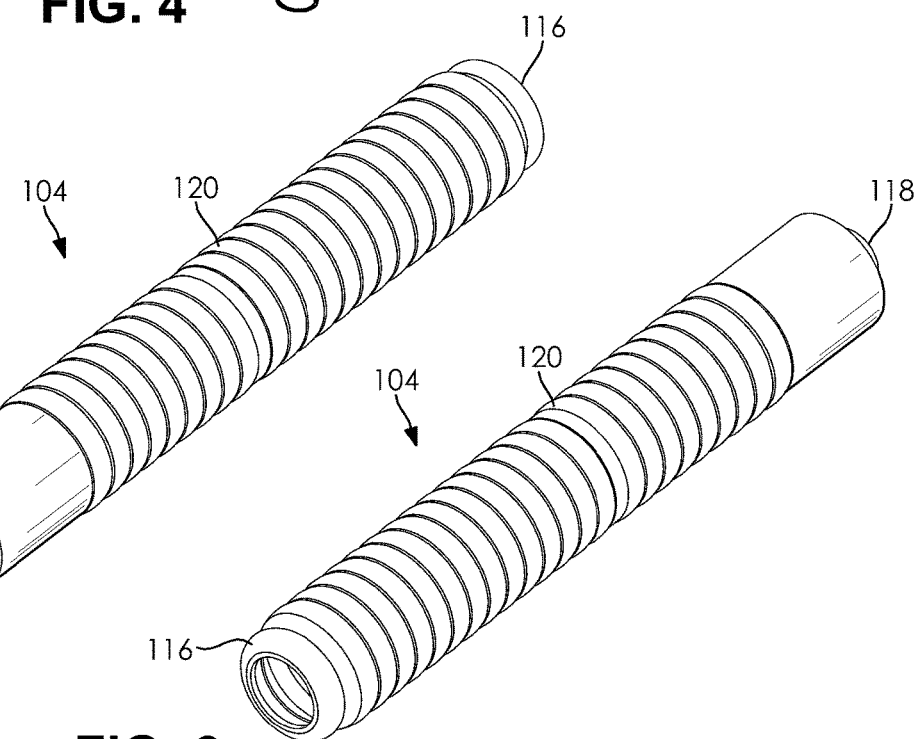
FIG. 5
FIG. 6

MALE EXTERNAL CATHETER

TECHNICAL FIELD

Various embodiments relate generally to external catheters.

BACKGROUND

Urinary catheters are medical devices configured to collect urine from the bladder. Internal and external urinary catheters may be used during treatment of urinary tract issues including urinary incontinence and incomplete bladder emptying. In some examples, a medical professional may apply an external catheter to a male patient, for example, to manage urinary incontinence by diverting urine to a bag located external to the patient's body.

Certain urinary tract conditions may be treated through the use of internal or external collection devices. Internal collection devices, for example, urethral catheters are commonly used in medical practice. However, in some scenarios, urethral catheterization is challenging and sometimes fails. For example, urethral catheters are difficult or altogether impossible to apply to morbidly obese patients having a buried penis with scrotal edema. I. Alnadhari, O. Abdelja-leel, O. Ali, A. Shamsodini & M. Salah, *Urethral Catheterization of Buried Penis in Obese Patients: a Novel Technique and Literature Review*, National Center for Biotechnology Information (Oct. 28, 2018), https://www.ncbi.nlm.nih.gov/pubmed/30030726. Different devices and methods have been published and developed to overcome the difficulties associated with applying urethral catheters to obese patients having buried, retracted or retractive penises.

External collection devices, for example, external catheters, are typically more comfortable, less painful, and less restrictive on patient activity than other internal urine collection devices. Because external catheters are generally non-invasive devices, making the devices easier and less painful to apply, both patients and medical professionals have come to prefer the application of external catheters over internal catheters.

As a result, a variety of external catheters have been developed, including condom catheters, reusable body-worn urinals, and non-sheath glans-adherent external collection devices which are generally configured to adhere to patients' or users' external genitalia or pubic areas and collect urine output. MIKEL GRAY, CLAUDIA SKINNER, & WENDY KALER, *External Collection Devices as an Alternative to the Indwelling Urinary Catheter*, National Center for Biotechnology Information (May 13, 2016), https://www.ncbi.nlm.nih.gov/pmc/articles/PMC4870965/. However, in some scenarios, using or applying prior-developed external catheters may be challenging or altogether impossible, depending on the particular body type of the patient or user. For example, morbidly obese patients may present with a retracted, retractive, or buried penis, making it problematic or impossible to apply urethral or internal catheters and prior-developed external catheters to the patient, or requiring multiple re-applications of such catheters which are often misplaced or dislodged by the patient's abdomen.

Some prior developed external catheters are non-latex and latex-based sheath devices, such as the external catheter disclosed in U.S. Pat. No. 4,626,250, which provides a sheath configured to be applied to the tip of a patient's penis and rolled down the penile shaft. Some latex-based sheath devices, such as the Rusch Golden-Drain—Male External Latex Condom Catheter (with Foam Strap), include an adhesive foam strap for wrapping around the device to provide securement. Some non-latex based sheath devices, such as the Bard Rochester Catheter—Latex-free Male External Condom Catheter, include a foam Velcro® strap to wrap around the device and provide securement. Other non-latex based sheath devices, such as the Cook Medical Non-Adhesive Silicone Male External Condom Catheter, include an inflatable retention ring configured to secure the sheath catheter to the penis. All such non-latex and latex-based devices require appropriate and accurate sizing in order to adequately secure the device to the patient's penis. As such, medical professionals are required to locate and access the patient's penis in order to apply or secure the device to the patient's penis. Therefore, it is challenging or altogether impossible to apply these prior developed sheath devices to an obese patient whose penis may be buried, retracted or retractive, hindering or limiting access to the patient's penis, and making it difficult to use these devices with morbidly obese patients having a retracted, retractive, or buried penis.

Other prior developed external catheters include non-sheath, glans-adherent external catheters, such as the Men's Liberty Male External Catheter and the external catheter disclosed in U.S. Pat. No. 8,551,062, are used to externally catheterize obese male patients. These non-sheath, glans-adherent external catheters are applied by aligning the central hole of the device over a patient's external urethral meatus and firmly pressing a "faceplate" over the glans of the penis while a hydrocolloid seal is wrapped around the faceplate to ensure adherence. However, successful utilization of this device requires specialized, specific and proper application, necessitating a high level of dexterity. Therefore, adequately applying the device to an obese patient or user morbidly obese patients may present with a retracted, retractive, or buried penis presents many challenges, including the obstruction of the view of and access to the patient's penis. Moreover, because of the size, shape, and weight of an obese patient's abdomen, even if the glans-adherent external catheter is adequately applied, the device is configured to attach to the end of the user's penis, making the device susceptible to inadvertent dislodging or misplacing when acted upon by the weight of the patient's abdomen.

In another prior art approach, the Retracted Penis Pouch developed by Hollister Incorporated has an integrated hydrocolloid ring with an adhesive and collection pouch is applied by appropriately sizing the circumference of the hydrocolloid wafer barrier to fit the circumference of the patient's penis, applying the pouch over the penis, and adhering the adhesive to the pubis. However, this prior-developed external collection device also requires accurately locating the patient's retracted, retractive, or buried penis in order to apply the device. Even when the Retracted Penis Pouch can be applied to a retracted, retractive, or buried penis, the collection bag is apt to burst from the pressure of an a patient's abdomen thereby or be obstructed by the patient's abdomen constricting the flow of urine from the patient's penis into the urine collection bag.

Therefore, there is a need in the art for an external catheter that can be applied more easily to morbidly obese patients having a retracted, retractive, or buried penis that does not obstruct urine flow into the collection receptacle and does not suffer from problems of collection receptacle breakage as in prior art solutions. As discussed in more detail herein, a semi-rigid internal tube and a collection bag having an adhesive attachment member to provide a supported structure configured to connect and maintain the attachment of the external catheter to an area of pubic fat so that the internal tube is in fluid communication with urine flowing from a buried, retracted or retractive penis, and configured to prevent or reduce the rate of dislodgement or displacement of the external catheter is described. These and other features and advantages of the present invention will be explained and will become obvious to one skilled in the art through the summary of the invention that follows.

SUMMARY

Apparatus and associated methods relate to an external catheter configured with a urine collection bag having an internal tube adapted to fit and hold a male patient penis, providing supported connection to the patient body, and an adhesive having a removable non-adhesive backing to selectively and securely attach the urine collection bag to an area of pubic area fat where urine flows from a buried, retracted or retractive penis. In an illustrative example, the urine collection bag may be a transparent and flexible plastic material permitting visualization of the inner contents of the bag. The internal tube may be, for example, a semi rigid and flexible tube permitting supported connection to the pubic area, and specifically, configured to be inserted in a cavity or hole in pubic area fat so that the tube is in fluid communication with the urine output of patients or users having a retracted, retractive, or buried penis. In some examples, the semi rigid and flexible internal tube may be adapted to prevent the dislodging or misplacement of the external catheter or breakage of the urine collection bag by the patient's abdomen and prevent the collapsing of the thin-walled urine collection bag. Various examples may advantageously provide attachment to the pubic area fat by the adhesive disposed coincident to the outer circumference of the internal tube.

Various embodiments may achieve one or more advantages. For example, some embodiments may reduce the amount of effort traditionally required of a user or medical professional to apply an external catheter to the user's penis. For example, a medical professional may have difficulty applying prior-developed external catheters to an obese user's penis, and prior developed external catheters are easily dislodged by the size and shape of the patient's abdomen. Moreover, some prior developed external catheters lack a supported structure, for example, the support of a semi-rigid internal tube provided by the various embodiments of an external catheter disclosed herein. In an illustrative example, the semi rigid and flexible internal tube is configured to be inserted in a cavity or hole in pubic area fat so that the tube is in fluid communication with the urine output of patients or users having a retracted, retractive, or buried penis. In some examples, the internal tube is semi-rigid and configured to prevent the accidental removal or displacement of the device. In some scenarios, the external catheter may be utilized by users suffering from obesity, who have limited view or access to their penis, but otherwise have control of their bladder movements. For example, the adhesive may be applied to an area of pubic area fat while the internal tube is inserted into a cavity or hole in pubic area fat such that the internal tube is in fluid communication with the buried, retracted or retractive penis of the patient, to provide an accessible channel, providing the user with a means to easily direct the flow of their urine output. In an illustrative example, the urine expelled from the user's penis is in fluid communication with and is directed into the collection bag and through the internal tube to the drain, enabling the user to more directly control and guide the patient's urine output.

The details of various embodiments are set forth in the accompanying drawings and the description below. Other features and advantages will be apparent from the description and drawings, and from the claims.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

FIG. 1 is a top, front perspective view of an external catheter in accordance with an embodiment of the present invention.

FIG. 2 is a bottom, front perspective view of an external catheter in accordance with an embodiment of the present invention.

FIG. 3 is a cross sectional view of an external catheter in accordance with an embodiment of the present invention.

FIG. 4 is a top, front perspective view of an external catheter in accordance with an embodiment of the present invention.

FIG. 5 is a bottom, front perspective view of an internal tube of an external catheter in accordance with an embodiment of the present invention.

FIG. 6 is a top, front perspective view of an internal tube of an external catheter in accordance with an embodiment of the present invention.

DETAILED SPECIFICATION

Figure 7:
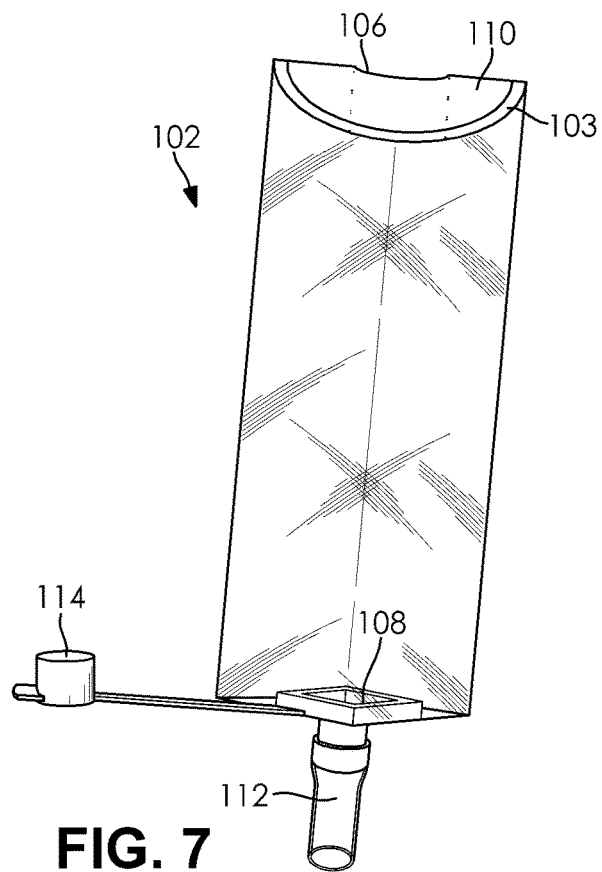
FIG. 7 is a top, front perspective view of a urine collection bag of an external catheter in accordance with an embodiment of the present invention.

The present invention generally relates to a medical device configured for use as an external catheter.

FIG. 1 depicts a top, front perspective view of an embodiment external catheter 100 in an illustrative assembled configuration. In FIG. 1, the exemplary assembled external catheter 100 includes the urine collection bag 102 having a first hole 106 at its first end and a second hole 108 at its second end. In the illustrated embodiment, the bag 102 defines a pocket for the collection and storage of urine. In the depicted embodiment, the bag 102 comprises a flexible plastic material. In some embodiments, the bag 102 is transparent and permits the viewing of stored urine.

FIG. 2 depicts a bottom, front perspective view of an external catheter 100 in accordance with an embodiment of the present invention. As shown in FIG. 2, the exemplary catheter 100 includes an internal tube 102 having a first opening 116 at its first end and a second opening 118 at its second end. In the depicted embodiment, the first hole 106 of the bag 102 receives the internal tube 102. In the illustrated embodiment, the internal tube 104 extends into the collection bag 102 and creates a channel adapted to direct urine to the second end of the collection bag 102. As shown in FIG. 1, the second end of the collection bag 102 may receive the second opening 118 of the internal tube. In some embodiments, the second opening 118 of the internal tube 102 tapers at the second end.

FIG. 3 is a cross sectional view of an external catheter 100 in accordance with an embodiment of the present invention. As shown in FIGS. 3, in accordance with embodiments of the present invention, a drain 112 may be coupled to the second hole 108. In the illustrated embodiment, the drain 112 includes a drain valve 114. In the depicted embodiment, the drain valve 114 is linked to the drain 112. In some examples, the drain valve 114 is configured to selectively cover the drain 112.

FIG. 4 is a top, front perspective view of an external catheter 100 in accordance with an embodiment of the present invention. As shown in FIG. 4, the first hole 106 of the collection bag 102 is adapted to receive the first end of the internal tube 104. In some embodiments, the second opening 118 of the internal tube 104 may be independent of second hole 108.

FIG. 5 is a bottom, front perspective view of an internal tube 104 of an external catheter 100 in accordance with an embodiment of the present invention. In the depicted embodiment, the internal tube 104 has a first opening 116 at its first end and a second opening 118 at its second end. In some embodiments, the internal tube 104 may include an elasticity element. In the depicted embodiment, the elasticity element is corrugated tubing 120 adapted to permit flexibility.

FIG. 6 is a top, front perspective view of an internal tube 104 of an external catheter 100 in accordance with an embodiment of the present invention. In the depicted embodiment, the internal tube 104 has a first opening 116 at its first end and a second opening 118 at its second end.

FIG. 7 is a top, front perspective view of a urine collection bag 102 of an external catheter 100 in accordance with an embodiment of the present invention. As shown in the embodiment illustrated in FIGS. 1-4 and 7, an adhesive element 103 is disposed around the opening of the first hole 106 and lines at least a portion of the top of the urine collection bag 102. In some embodiments, the adhesive element 103 is configured to attach the external catheter 100 to pubic area fat and the first opening 116 of the internal tube 104 is configured to be inserted into a cavity, hole, or channel in pubic area fat so that the first opening 116 of the internal tube 104 is in fluid communication with a buried, retracted or retractive penis. Preferably, the internal tube 104 is made of a material that will not irritate the cavity, hole, or channel into which the tube 104 is inserted. In some embodiments, the first opening 116 of the internal tube 104 could be coated or covered with a covering (not pictured) made of even softer material to prevent irritation at the point of insertion. In the illustrated embodiment, the adhesive element 103 has a removable non-adhesive backing 110. In some embodiments, the adhesive element 103 is a hydrocolloid wafer barrier. In some embodiments, the adhesive element 103 is a hydrocolloid skin barrier configured to permit one- to two-day wear time. In some examples, the adhesive element 103 may be used to sanitarily dispose the collection bag 102. For example, the adhesive element 103 may be utilized to close or seal the collection bag 102 and prevent any fluids from leaking from the first hole 106. In an illustrative example, the adhesive element 103 may be folded across its diameter to adhere a first half of the adhesive element 103 to a second half of the adhesive element 103 to create a fluid tight seal between the first hole 106, internal tube 104, and collection bag 102 so that urine does not leak.

Figure 8:
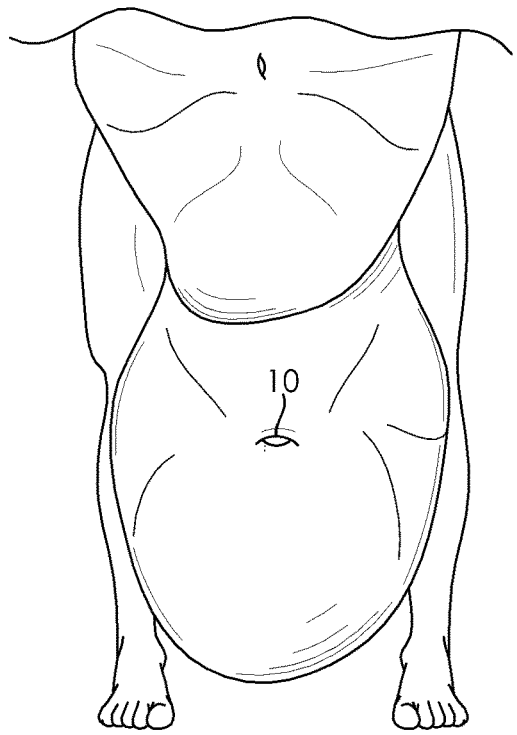
FIG. 8 is an exemplary illustration of an obese male external catheter user.
Figure 9:
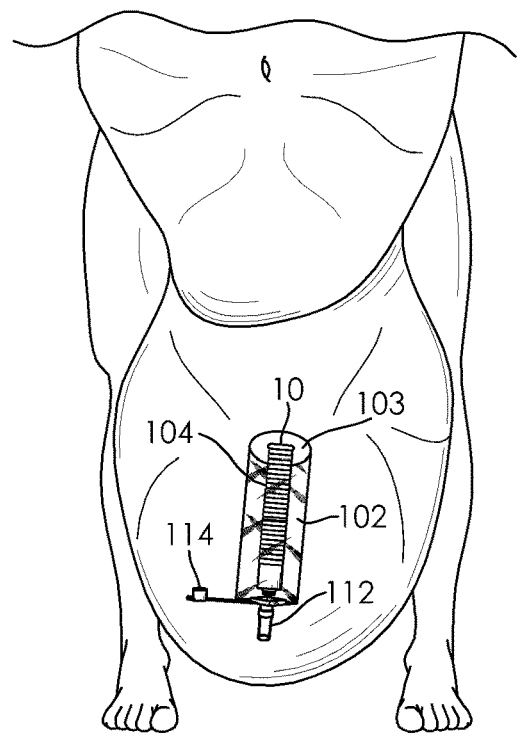
FIG. 9 is an exemplary usage scenario of an external catheter applied to an obese male user in accordance with an embodiment of the present invention.

FIGS. 8-9 depict an exemplary usage scenario in which an external catheter is applied to a male user in accordance with an embodiment of the present invention. In the illustrated example, the external catheter 100 is applied to a male patient by cleaning the area to which the adhesive element will be applied, for example, by rinsing or shaving the area to ensure consistent securement of the device 100 to the patient's body and prevent urine or odor leakage from the collection bag 102. Next, the adhesive element 103 is applied to the pubic area fat of the patient which is in close proximity to or in fluid communication with urine streaming from a buried, retractive or retracted penis. In the depicted example, the semi-rigid and flexible internal tube 104 provides structured support to the thinly-walled collection bag, preventing the accidental removal or displacement of the device from under the patient's stomach. In some examples, the internal tube 104 is flexible to avoid the accidental piercing or tearing of the collection bag. In the illustrated example, the internal tube 104 is placed in a pocket or channel or cavity 10 of an obese patient's stomach, in a location where the first hole 106, internal tube 104, and collection bag 102 are in fluid communication with urine streaming from a buried, retracted or retractive penis, such that any urine expelled from the patient is collected into the collection bag 102, directed through the internal tube 104 and into the drain 112, which may be optionally connected directly to the second end of the internal tube 104. In some scenarios, urine is stored in the collection bag 102 when the drain valve 114 is closed, and urine may be decanted from within the collection bag 102 when the drain valve 114 is open.

In an illustrative example, the external catheter is applied to an obese patient by removing the non-adhesive backing to expose the adhesive element, moving the patient's abdomen to provide access to the area out of which urine flows, and securing the collection bag to the pubic area. In some embodiments, identifying the precise location of the penis is not necessary because the external catheter simply needs to be applied to a general location where a buried, retracted or retractive penis is suspected to be, in fluid communication with urine flowing from the buried, retracted or retractive penis. In some embodiments, as the external catheter is applied to the area of pubic fat, the internal tube is placed in fluid communication with urine streaming from a buried, retracted or retractive penis, and directs urine to the drain, to eventually empty the collection bag or decant the collected urine into a leg pouch. Even as the patient's abdomen is released, the external catheter device maintains its position, having been secured to the patient's pubic fat area by the adhesive element and having structural support provided by the semi-rigid and flexible internal tube. The structural support and flexibility of the internal tube, in conjunction with adhesion of the adhesive element to the patient's pubic area prevents the inadvertent dislodging or misplacement of the device. Moreover, the internal tube is configured to provide sufficient flexibility to account for the patient's voluntary movements or activities and to avoid the accidental piercing or tearing the collection bag. Furthermore, the semi-rigid internal tube may prevent the compression forces applied by the patient's abdomen from flattening the collection bag of the external catheter and obstructing or otherwise constricting the path of urine from the patient's penis.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of" In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112

(f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An external urinary catheter device and collection system comprising:
    a semi-rigid and substantially tubular hollow body member beginning at a first end and terminating at a second end, the tubular hollow body defining a channel having a first opening at the first end configured to direct the flow of urine to a second opening at the second end;
    a substantially flexible and thin-walled collection bag adapted to substantially retain at least a portion of the tubular hollow body, the collection bag having a first hole adapted to receive the first end of the tubular hollow body and a second hole adapted to receive the second end of the tubular hollow body and configured to function as a drain to permit the decanting of urine from the collection bag; and
    an adhesive element disposed around the first hole, the adhesive element configured to secure the tubal hollow body member of the external catheter device to a cavity, channel, or hole in pubic fat that is in fluid communication with urine streaming from a buried, retracted or retractive penis;
    wherein at least a portion of the first end of the tubular hollow body extends outward of the adhesive element, a distance that is a length sufficient to be inserted into the cavity, channel, or hole in pubic fat past the first hole of the collection bag.

2. The external urinary catheter device and collection system of claim 1, wherein the tubular hollow body is flexible and a fluid tight seal is created between the first hole, internal tube, and collection bag so that urine does not leak from the catheter device and collection system.

3. The external urinary catheter device and collection system of claim 1, wherein the tubular hollow body includes an elasticity element.

4. The external urinary catheter device and collection system of claim 3, wherein the elasticity element is corrugated tubing adapted to permit flexibility.

5. The external urinary catheter device and collection system of claim 1, wherein the adhesive element includes a removable non-adhesive backing.

6. The external urinary catheter device and collection system of claim 1, wherein the adhesive element is a hydrocolloid wafer barrier.

7. The external urinary catheter device and collection system of claim 1, wherein the drain is adjustable between an open and closed position.

8. The external urinary catheter device and collection system of claim 7, wherein a valve transitions the drain between the open and closed positions.

9. A method of applying an external urinary catheter device and collection system to a patient, the catheter comprising a semi-rigid and substantially tubular hollow body member defining a channel having a first opening configured to direct the flow of urine to a second opening, a collection bag adapted to substantially retain at least a portion of the tubular hollow body, and an adhesive element disposed at a first hole of the collection bag, comprising the steps of:
    locating a cavity in a pubic area from which urine streams and in which a buried, retracted or retractive penis is suspected to be disposed;
    positioning the tubular hollow body in the cavity such that it is in fluid communication with the urine streaming from the buried, retracted or retractive penis; and
    applying the adhesive element around the cavity so as to secure the tubular hollow body within the cavity, such that any urine expelled from the user is directed through and into a drain disposed at the second opening of the tubular hollow body.

10. The method of claim 9 in which there is the further step of cleaning the area around the cavity to which the adhesive element will be applied to provide consistent securement of the device to the user body and a fluid tight seal is created between the first hole, internal tube, and collection bag so that urine does not leak from the catheter device and collection system.

11. The method of claim 9 in which there is the further step of attaching the drain to a leg pouch configured to store the urine expelled from the catheter device.

12. The external urinary catheter device and collection system of claim 1, wherein the adhesive element is specifically configured to secure the external catheter device to a cavity, channel, or hole in pubic fat that is in fluid communication with urine streaming from a buried, retracted or retractive penis.

13. The external urinary catheter device and collection system of claim 1, wherein the adhesive element does not attach directly onto a penis.

14. The external urinary catheter device and collection system of claim 1, wherein at least a portion of the first end of the tubular hollow body extends outward of the collection bag a distance past the first hole of the collection bag.

15. The external urinary catheter device and collection system of claim 1, wherein upon application of the adhesive element to a body, at least a portion of the first end of the tubular hollow body extends into the cavity, channel, or hole in pubic fat that is in fluid communication with the buried, retracted or retractive penis.

* * * * *